United States Patent [19]

Nathansohn et al.

[11] 4,440,764
[45] Apr. 3, 1984

[54] WATER SOLUBLE ESTERS OF STEROID-OXAZOLE AND PHARMACEUTICAL COMPOSITIONS CONTAINING THEM

[75] Inventors: Giangiacomo Nathansohn; Giorgio Winters, both of Milan, Italy

[73] Assignee: Gruppo Lepetit S.p.A., Milan, Italy

[21] Appl. No.: 258,098

[22] Filed: Apr. 27, 1981

[30] Foreign Application Priority Data

Apr. 28, 1980 [IT] Italy ............................... 21671 A/80

[51] Int. Cl.$^3$ ........................................... A61K 31/58
[52] U.S. Cl. .................................. 424/241; 260/239.5
[58] Field of Search ....................... 260/239.55, 397.45, 260/239.5; 424/241

[56] References Cited

U.S. PATENT DOCUMENTS 2,656,366 10/1953 Minlon ........................... 260/397.45
3,436,389 4/1969 Nathansohn et al. .......... 260/397.45
3,461,119 8/1969 Nathansohn et al. .......... 260/397.45

*Primary Examiner*—Elbert L. Roberts
*Attorney, Agent, or Firm*—William J. Stein; Raymond A. McDonald; Gary D. Street

[57] ABSTRACT

Water-soluble esters of steroid-oxazole derivatives of formula I

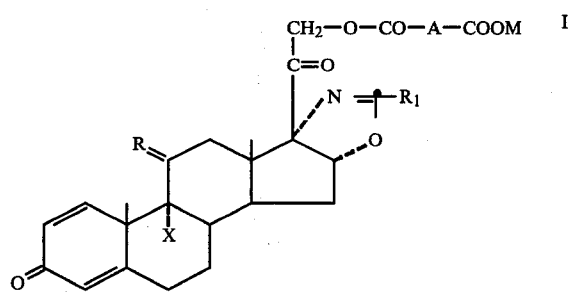

wherein R is O or a H, (β-OH) group, $R_1$ is hydrogen, lower alkyl or phenyl, X is hydrogen, fluorine or chlorine, A stands for a direct carbon-carbon bond or a hydrocarbon chain containing from 1 to 4 carbon atoms, and M is hydrogen or a pharmaceutically acceptable cation are described as well as pharmaceutical compositions containing them particularly suitable for parenteral administration.

3 Claims, No Drawings

WATER SOLUBLE ESTERS OF STEROID-OXAZOLE AND PHARMACEUTICAL COMPOSITIONS CONTAINING THEM

Water-soluble esters of steroids are widely employed in therapy. More particularly they are used for the parenteral administration of steroid molecules. As an example, prednisolone, hydrocortisone or 6α-methyl prednisolone succinate sodium salts are employed for this purpose. Steroid-oxazoles and their esters with lower aliphatic acids are described in U.S. Pat. Nos. 3,436,389 and 3,461,119.

The present invention refers to water-soluble esters of steroid-oxazole derivatives of formula I

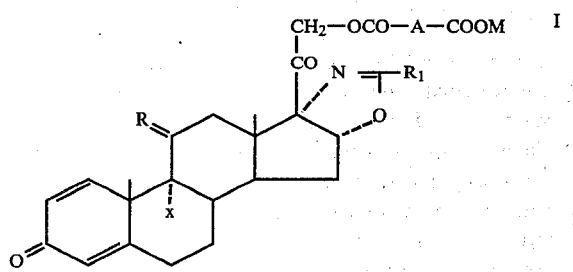

wherein R is O or a H,(β—OH) group, $R_1$ is hydrogen, lower alkyl or phenyl, X is hydrogen, fluorine or chlorine, A stands for a direct carbon-carbon bond or a hydrocarbon chain containing from 1 to 4 carbon atoms, and M is hydrogen or a pharmaceutically acceptable cation. As used herein the term "lower alkyl" designates a straight or branched alkyl radical of from 1 to 4 carbon atoms; the term "hydrocarbon chain" is intended to designate a straight alkylene or alkenylene chain of from 1 to 4 carbon atoms; and the term "pharmaceutically acceptable cation" refers to organic or inorganic cations which do not affect the pharmacological properties of the free acid and do not produce toxic or undesired side effects. Examples of such pharmaceutically acceptable cations are for instance the following ones: sodium, potassium, calcium, magnesium, ammonium and organic cations such as alkylammonium, di-alkylammonium, tri-alkylammonium, tetra-alkylammonium, di-hydroxyalkylammonium, tri-hydroxyalkylammonium and alkylbenzylammonium. More specific examples of organic cations includes those cations deriving from the salification of the free acid with one of the following amines: ethylamine, di-ethylamine, triethylamine, pyrrolidine, piperidine, morpholine, lysine, arginine, procaine, ethanolamine, piperazine, N-methylpiperazine, N-benzyl-N-methylamine, diethanolamine, ethylenediamine, N,N'-dibenzylethylenediamine, N-methylglucamine, and 2-amino-2-methyl-1-propanol.

A preferred group of compounds of formula I comprises those compounds wherein R is O or a H(β—OH) group, $R_1$ is lower alkyl, X is hydrogen or fluorine, A is an alkylene chain of from 1 to 4 carbon atoms and M is hydrogen or a pharmaceutically acceptable cation. A most preferred group of compounds of formula I comprises those compounds wherein R is O or a H(β—OH) group, $R_1$ is lower alkyl, X is hydrogen or fluorine, A is ethylene and M is hydrogen or sodium. The compounds of the present invention are prepared according to the usual methods known in this field for the esterification of steroids having a free hydroxy function at C-21.

More particularly the compounds of formula I may be prepared starting from the corresponding 21-hydroxy steroid-oxazole of formula II

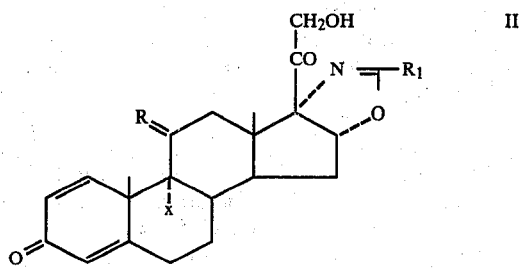

wherein R, $R_1$ and X are as previously defined, through reaction with a dicarboxylic acid derivative of formula III

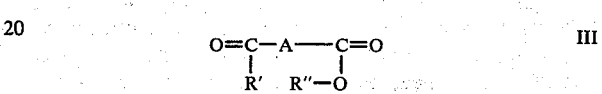

wherein A is as defined above, R' is hydroxy or a halogen atom, typically chlorine or bromine, and R" is an easily removable protecting group of the carboxylic function or, when A is a hydrocarbon chain of at least two carbon atoms, R' is nil and R" is a direct bond between the oxygen atom and the carbon atom of the other C=O group so as to form a cyclic anhydride of the dicarboxylic acid. The esterification is carried out according to usual procedures which are entirely familiar to any skilled chemist and affords, with previous deprotection of the terminal carboxylic group when R" is a blocking group, compounds of formula I wherein R, $R_1$, X, and A are as previously defined and M is a hydrogen atom. These compounds, if desired, may then be transformed into the corresponding pharmaceutically acceptable salts by conventional salification procedures. More particularly, according to a general method, the compounds of formula I wherein M is hydrogen are prepared by reacting the corresponding alcohols II with a mono-ester derivative of a dicarboxylic acid or of the corresponding mono-acyl halide, and when the esterification of the 21-hydroxy group is completed, regenerating the terminal carboxylic group under conditions which do not affect the other sensitive groups in the end molecule. A range of ester groups may suitably be employed to protect one of the carboxylic groups of the dicarboxylic acid, and preferably the simple alkyl esters, typically the methyl, ethyl, or t-butyl esters, which may be easily cleaved at the end of the reaction by mild basic treatment. Dicarboxylic acids which may be used for the purpose of the present invention include oxalic, malonic, succinic, pimelic, adipic, maleic, and fumaric acid. The reaction is carried out in the presence of an organic solvent which is capable of dissolving the acid derivative and the steroid substrate without interfering with the reaction course such as for instance acetone, ethylacetate, halogenated lower aliphatic hydrocarbons, dimethylformamide, acetonitrile and the like. When a compound of formula III is employed wherein R' is a hydroxy group, the reaction is carried out, as known in the art, in the presence of a dehydrating agent, typically dicyclohexyl carbo-diimide or N,N'-carbonyldiimidazole, while, when a compound of formula III is used wherein R' is a halogen atom, the reaction is preferably carried out in the presence of an organic nitrogen base to combine with the hydrohalide which is formed. In this latter case the use of solvents which also act as bases is preferred. Examples of such preferred solvents are pyridine, and its C-methylated analogs as collidine, picoline, and their mixtures.

However, according to a preferred embodiment of the present invention, when A is a hydrocarbon chain of at least two carbon atoms, the esterification of the 21-hydroxy group of the steroid-oxazole II is carried out by reacting the alcohol II with the cyclic anhydride of the dicarboxylic acid in an organic solvent in the presence of a basic catalyst. This procedure in fact allows direct formation of compounds I wherein M is hydrogen without needing any additional deprotection step. In both cases when a compound I is desired wherein M is a pharmaceutically acceptable cation, it may be prepared from the corresponding acid thus obtained, by conventional procedures.

Organic solvents which may suitably be employed in this reaction are those seen above i.e., halogenated lower aliphatic hydrocarbons, acetone, ethyl acetate, dimethylformamide, acetonitrile and the like, while 4-(N,N-dimethylamino)pyridine is a preferred basic catalyst. Alternatively basic solvents such as pyridine, collidine, picoline and their mixtures, may conveniently be employed to act both as the reaction solvent and the basic agent. The reaction is carried out at a temperature comprising between $-15°$ C. and $40°$ C., using excess anhydride over the stoichiometric amount. This excess may range from about 0.1 to about 5 molar proportions of the starting steroid-oxazole II. The obtained product is then recovered according to the usual procedures which are entirely familiar to any skilled chemist. Said procedures generally comprise washing the reaction mixture with a diluted acid solution and water and then crystallizing the end product from a suitable solvent. When a basic organic solvent is employed, the end product is preferably recovered by pouring the reaction mixture in aqueous mineral acids, separating the solid, and purifying the obtained ester by dissolving it in an aqueous basic solution, separating the insoluble organic residue by extraction with an organic solvent immiscible with the aqueous basic solution, and recovering the product in the form of the free acid by acidifying the basic solution with diluted mineral acids, optionally followed by the extraction of the product with an organic solvent. The product thus obtained may then be crystallized from a suitable solvent.

When a compound I is desired wherein M is a pharmaceutically acceptable cation, it may be isolated directly as reaction product by neutralizing a solution of the free acid with the suitably selected base or the corresponding carbonate or bicarbonate.

The compounds of the present invention have been shown to be highly effective in the pharmacological tests carried out for determining their therapeutic activity.

As an example, the carrageenin-induced oedema test in rats (i.v.) 11$\beta$,21-dihydroxy-2'-methyl-5'H-pregna-1,4-dieno[17,16-d]oxazole-3,20-dione-21-hemisuccinate (deflazacort 21-hemisuccinate) was found to be 15 and 142 times more active then prednisolone hemisuccinate and hydrocortisone hemisuccinate respectively. In the Nystatin-induced oedema test, administering by i.v. route antiinflammatory equivalent doses of deflazacort hemisuccinate, prednisolone hemisuccinate and hydrocortisone showed that deflazacort hemisuccinate, at the 48th, 72nd, and 96th hours, had a longer lasting antiphlogistic activity than the reference compounds. In the protection against anaphylactic shock and endotoxin shock in mice, the following results have been obtained:

|  | Anaphylactic shock $ED_{50}$ (mg/Kg i.p.) | Endotoxin shock $ED_{50}$ (mg/Kg s.c.) |
| --- | --- | --- |
| Deflazacort hemisuccinate | 22 | 31 |
| Prednisolone hemisuccinate | 35.5 | 50.5 |
| Hydrocortisone hemisuccinate | 143 | 180 |

Remarkably favorable results have been obtained also in testing the hepatic neoglycogenetic activity in adrenalectomized rats (deflazacort hemisuccinate showed to be about 5 and 40 times more potent than prednisolone hemisuccinate and hydrocortisone hemisuccinate respectively). The evaluation of the mineralocorticoid effects in the adrenalectomized rats showed that deflazacort hemisuccinate, at doses which provide the same pharmacological effect, affects the equilibrium sodium-potassium much less than prednisolone or hydrocortisone hemisuccinate.

The compounds of the present invention are particularly useful for the preparation of pharmaceutical dosage forms for parenteral administration, which are generally used in anti-shock, anti-allergic immuno-suppressive and intra-articular therapy. Besides a therapeutically effective amount of a compound of formula I, these preparations contain a physiologically acceptable aqueous vehicle and may be used either in the form of solutions ready for injection or dry soluble products to be combined with the aqueous solvent just prior to use. In the former case, the solution may contain stabilizing and preservative agents such as for instance thioglycerol, thioglycolic acid, sodium citrate, and ethylenediaminetetracetic acid di-sodium salt. The aqueous vehicle generally consists of pyrogen-free twice-distilled water or mixtures of pyrogen-free twice-distilled water and aliphatic glycols, such as propylene glycol and polyethylene glycols. These solutions generally have isotonicity and pH physiologically compatible with the human body.

In the latter case, the active principle is generally employed in the form of lyophilized pharmaceutically acceptable salt.

The amount of therapeutically active steroid-oxazole compound in the dosage unit forms depends on the compound of formula (I) employed and on the type of treatment applied for. Generally, parenteral dosage units contain from 1 to 200 mg of active ingredient. More particularly, dosage units for intra-articular treatment contain lower amounts of active principle, such as from 1 to 60 mg while dosage units for intramuscular, subcutaneous or intravenous injections contain higher amounts of active ingredient, typically from 15 to 200 mg.

The following examples describe in more detail some embodiments of the present invention without limiting its scope.

EXAMPLE 1

Preparation of 11β, 21-dihydroxy-2'-methyl-5'H-pregna-1,4-dieno[17,16-d]oxazole-3,20-dione 21-hemisuccinate (I, R=H (β—OH), $R_1$=—$CH_3$, X=H, A=—$CH_2$—$CH_2$—, and M=H)

Succinic anhydride (3.75 g) is added at 10° C. to a stirred solution of 11β, 21-dihydroxy-2'-methyl-5'H-pregna-1,4-dieno[17,16-d]oxazole-3,20-dione (9.98 g) in methylene chloride (70 ml).

Then p-dimethylaminopyridine (0.305 g) is added and the mixture is allowed to react at room temperature for 24 hours. The formation of the compound of the title may be followed by thin-layer chromatography on silicagel plates using a chloroform:methanol 9:1 mixture as the eluting system.

When the reaction is completed, the final solution is washed first with 1% aqueous HCl (20 ml) and then with water, dried over sodium sulfate and diluted with toluene (70 ml).

The low boiling solvent is distilled off whereupon the compound of the title crystallizes. The suspension is cooled to 0° C. for two hours and 10.82 g of the desired product is collected. Concentration of the mother liquors to 5–10 ml under reduced pressure and cooling yields a further crop of gummy crystals. This solid is ground with a few ml of hot toluene and collected yielding further 0.54 g of the compound of the title. Overall yield 91%. M.p. 240° C.

EXAMPLE 2

Preparation of 11β,21-dihydroxy-2'-methyl-5'H-pregna-1,4-dieno[17,16-d]oxazole-3,20-dione 21-hemisuccinate (I,R=H (β—OH), $R_1$=—$CH_3$, X=H, A=—$CH_2$—$CH_2$—, M=H)

To a stirred solution of finely ground succinic anhydride (76.9 g) in dry pyridine (380 ml), 11β,21-dihydroxy-2'-methyl-5'H-pregna-1,4-dieno[17,16-d]oxazole-3,20-dione (76.9 g) is added portionwise at −10° C. After 30 minutes the temperature is allowed to rise to 20° C. and stirring is continued for 20 hours. The reaction mixture is then poured into ice-cold 10% sulfuric acid (1 l.) The gummy solid which precipitates is collected and dissolved in 5% aqueous $NaHCO_3$. The aqueous solution thus obtained is extracted with ethyl ether which is then discarded, while the remaining aqueous layer is acidified with 10% hydrochloric acid. The solid which precipitates is extracted twice with ethyl acetate (500 ml) and the organic phase is washed with water, dried over sodium sulfate and evaporated to dryness. The residue is treated with ethyl ether (200 ml) and then filtered, yielding 82 g of the compound of the title. The mother liquors are evaporated to dryness and treated again with ethyl ether yielding further 8 g of the end product. Overall yield: 93.5%. The compound of the title melts at 240° C.; $[\alpha]_{20}^{D}$=+81 (C=0.53% in $CHCl_3$). The elemental analysis data and the I.R., $^1H$ NMR and mass spectra confirm the assigned structure. The starting 11β,21-dihydroxy-2'-methyl-5'H-pregna-1,4-dieno[17,16-d]oxazole-3,20-dione, m.p. 227°–9° C., is obtained by hydrolysis of the corresponding 21-acetate (98 g) dissolved in a mixture of methanol (1750 ml) and methylene chloride (580 ml) with 1 N NaOH (245 ml) (15 minutes at 0° C.).

The product obtained by distilling the solvent, extracting the residue with methylene chloride (1400 ml) and evaporating off the organic solvent, is purified by crystallization from boiling acetone (300 ml) by the addition of n-hexane (150 ml).

The sodium salt of deflazacort hemisuccinate which may conveniently be employed in parenteral formulations is prepared by suspending deflazacort hemisuccinate in water, neutralizing the suspension with the stoichiometric amount of 2% sodium hydroxide and lyophilizing the thus obtained solution.

We claim:

1. 11β,21-dihydroxy-2'-methyl-5'H-pregna-1,4-dieno[17,16-d]-oxazole-3,20-dione-21-hemisuccinate or a pharmaceutically acceptable salt thereof.

2. 11β,21-dihydroxy-2'-methyl-5'H-pregna-1,4-dieno[17,16-d]-oxazole-3,20-dione-21-hemisuccinate sodium salt.

3. A pharmaceutical composition for parenteral administration which contains 11β,21-dihydroxy-2'-methyl-5'H-pregna-1,4-dieno[17,16-d]oxazole-3,20-dione-21-hemisuccinate or a pharmaceutically acceptable salt thereof, as the active ingredient in combination with a pharmaceutically acceptable carrier.

* * * * *